United States Patent [19]

Anderson et al.

[11] Patent Number: 5,026,873
[45] Date of Patent: Jun. 25, 1991

[54] PROCESS FOR DIRECT ISOLATION OF CAPTOPRIL

[75] Inventors: Neal G. Anderson, Somerset; David A. Lust, Roosevelt; Barbara J. Bennett, North Brunswick, all of N.J.; Alan F. Feldman, Philadelphia, Pa.; Robert E. Polomski, Franklin Park, N.J.

[73] Assignee: E. R. Squibb & Sons, Inc., Princeton, N.J.

[21] Appl. No.: 432,028

[22] Filed: Nov. 6, 1989

[51] Int. Cl.⁵ .............................. C07D 207/08
[52] U.S. Cl. .............................. 548/533; 548/530
[58] Field of Search ............................. 548/533

[56] References Cited

U.S. PATENT DOCUMENTS

| | | | |
|---|---|---|---|
| 4,105,776 | 8/1978 | Ondetti et al. | 514/423 |
| 4,241,076 | 12/1980 | Ondetti et al. | 514/422 |
| 4,297,282 | 10/1981 | Ohashi et al. | 548/533 |
| 4,332,725 | 6/1982 | Fischer et al. | 548/533 |
| 4,332,726 | 6/1982 | Korzun | 548/533 |
| 4,460,780 | 7/1984 | Ohashi et al. | 548/201 |
| 4,668,798 | 5/1987 | Kim | 548/533 |

OTHER PUBLICATIONS

Shimazaki et al., Synthesis of Captopril Starting from an Optically Active β-Hydroxy Acid, Chem. Pharm. Bull. 30(9), 3139–3146 (1982).

*Primary Examiner*—Joseph Paul Brust
*Assistant Examiner*—Jacqueline Haley
*Attorney, Agent, or Firm*—Timothy J. Gaul

[57] ABSTRACT

A process is disclosed for direct isolation of captopril from a substrate of the formula

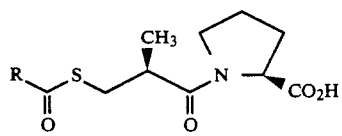

wherein R is lower alkyl or lower alkoxy. In this process, the substrate is first treated with an aqueous alkali metal hydroxide capable of forming a water-soluble salt of the substrate, wherein the alkali metal hydroxide has a concentration of 4M or greater. The substrate is then neutralized, preferably with a mineral acid. By this process, captopril may be directly crystallized from an aqueous solution, avoiding the prior art use of organic solvents and zinc treatment to reduce levels of sulfide and disulfide impurities, respectively. In an alternative embodiment, neutralization is carried out by use of a hydrogen-supplying ion exchange resin.

26 Claims, No Drawings

PROCESS FOR DIRECT ISOLATION OF CAPTOPRIL

FIELD OF THE INVENTION

This invention relates to processes for making the angiotensin converting enzyme (ACE) inhibitor captopril.

Background of the Invention

Captopril (Capoten ®) is a widely marketed ACE inhibitor useful as a cardiovascular agent. Preparation of captopril is described in U.S. Pat. No. 4,105,776 (issued Aug. 8, 1978). Captopril may be described by the structure

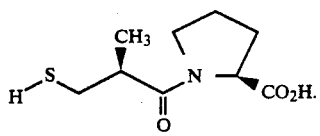

I

U.S. Pat. No. 4,668,798 describes a process for making captopril from a substrate of the formula

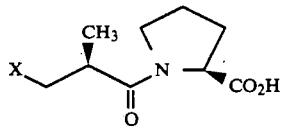

A wherein X is chlorine or bromine. In that process, carbon disulfide is reacted with a urea of the formula

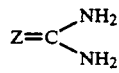

B in the presence of an alkali metal base to form the compound

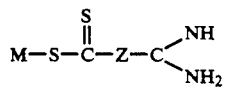

C wherein M is alkali metal and Z is oxygen or sulfur. Compound C is then reacted with Compound A, and the resulting product is hydrolyzed to form captopril in the reaction mixture. Thereafter, the reaction mixture is extracted a number of times with methylene chloride or ethyl acetate, treated with zinc powder to remove sulfide contaminants, and the resulting crude captopril is crystallized from an organic solvent.

U.S. Pat. No. 4,460,780 describes a process for making captopril using the substrate

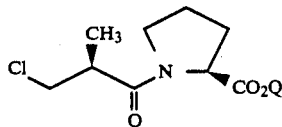

D wherein Q is hydrogen, sodium, potassium, or ammonium. In a reaction sequence similar to the above-described process, substrate D is reacted with an alkali trithiocarbonate and then hydrolyzed with an acid. The resulting product is dissolved in sulfuric acid, treated with zinc powder to remove disulfide impurities, and crystallized from an organic solvent to remove the sulfide impurity.

The preparation of captopril from substrates A and D requires the use of a sulfur-transfer reagent such as compound B or C. Many such reagents are prone to undergo oxidation-reduction reactions with compounds containing sulfur moieties, leading to the formation of disulfide and other impurities. A second source of disulfide impurity, however, is reaction of captopril with molecular oxygen according to the formula:

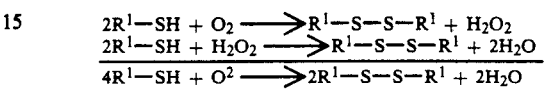

wherein $R^1$ is the remainder of captopril, having the structure

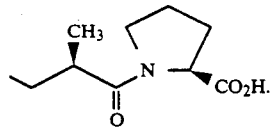

A number of other processes are available for the preparation of captopril, but these processes inherently form disulfide and other impurities and require the additional step of removing these impurities by treatment with zinc powder at low pH or some other similar method. See Shimazaki et al., *Chem. Pharm. Bull.* 30 (9), 3139-3146 (1982). In addition, these processes also involve the use of organic solvents such as methylene chloride, which may carry through in trace amounts into the final products. Such organic solvents may have undesirable properties for products for human consumption and so should be avoided. Also, the extraction of captopril into an organic solvent, the separation and distillation of that solvent to isolate the crude captopril, and its subsequent crystallization are time-consuming and require valuable manufacturing equipment and capacity.

BRIEF DESCRIPTION OF THE INVENTION

A process has now been discovered whereby captopril may be prepared without the need of treatment with zinc and sulfuric acid or other methods to remove disulfide impurities and without the use of any organic solvent for purification and crystallization. The process comprises reacting a compound of the formula

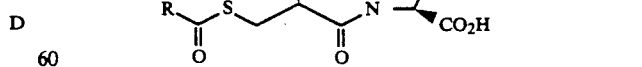

II wherein R is lower alkyl or lower alkoxy with an aqueous solution of an alkali metal hydroxide wherein the alkali hydroxide has a concentration of 4M or greater. The reaction mixture is then neutralized to give a concentrated solution of the alkali salt of captopril, the compound $R\text{-}COO^{\ominus}M^{\oplus}$ (e.g., sodium acetate) and excess alkali hydroxide (e.g., sodium hydroxide). Upon acidification with mineral acid (such as hydrochloric acid) captopril is produced in a concentrated solution of salt (e.g., NaCl). The solubility of oxygen, which oxidizes captopril to the undesired disulfide impurity, is much lower in concentrated salt solution than in water or dilute salt solutions. Therefore, the risk of the undesired oxygen side reaction (see Background of the Invention) is minimized throughout subsequent processing, whereas the captopril product precipitates and is collected. No further treatment is needed. Neutralization by addition of a mineral acid is preferred. Alternatively, the neutralization can be effected via a hydrogen-supplying ion exchange resin.

DETAILED DESCRIPTION OF THE INVENTION

The term "lower alkyl" refers to straight and branched chain hydrocarbon groups having 1 to 4 carbon atoms. Exemplary lower alkyl groups are methyl, ethyl, propyl, isopropyl, butyl, t-butyl, and isobutyl.

The term "lower alkoxy" refers to a lower alkyl group linked to an oxygen atom.

The term "alkali metal hydroxide" refers to NaOH, LiOH, and KOH. NaOH is the preferred alkali metal hydroxide.

A substrate of formula II may be prepared as described in U.S. Pat. No. 4,105,776. Although any formula II compound is a suitable substrate for the process, a substrate wherein R is methyl is preferred.

A substrate of formula II may be treated with an alkali metal hydroxide to yield compounds of the formulas

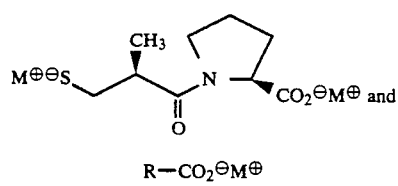

IIIa $$R-CO_2^{\ominus}M^{\oplus}$$ IIIb wherein $M^{\oplus}$ is an alkali metal ion (e.g., $Na^+$). An inert atmosphere (e.g., nitrogen or argon) is preferred for this part of the process. The temperature for hydrolysis is about $-10°$ to $50°$ C., with a temperature no higher than $45°$ C. preferred. The formula II compound is reacted with 2.5 to 5 molar equivalents, preferably about 3.3 molar equivalents, of alkali metal ions.

The concentration of the alkal metal hydroxide solution is an important factor in optimizing the yield of captopril salt (compound, IIIa). It has been found that alkali metal hydroxide concentrations of greater than or equal to 4M minimize the volume of the reactants and maximize the crystallization of captopril. At alkali metal hydroxide concentrations less than 4M, much of the captopril will remain in solution after acidification rather than crystallize, and the crystallized captopril will be mixed with high levels of disulfide impurity due to oxidation by dissolved molecular oxygen. The present process, in contrast, employs a concentrated salt solution that minimizes the solubility of oxygen, thus protecting against oxidation to the disulfide impurity. Cf. S. D. Cramer, Ind. Eng. Chem. Process Des. Dev. 19 (1980) 300. Concentrations of about 4 to 18M alkali metal hydroxide are suitable, but the most preferred concentration is about 9.5M.

The captopril salt (compound IIIa) is then neutralized. It is preferred that this neutralization be effected by acidification with a mineral acid. It is further preferred that acidification be carried out at a pH at which the captopril product crystallizes rather than oils out of the aqueous solution. It has been found that acidification directly to a pH of about 3.5 to 4.5 is preferable (3.9 is most preferred) to ensure good crystal growth. To optimize the crystallization of captopril, the reaction mixture may be further acidified, preferably to a pH less than or equal to about 3. It has been found that such further acidification may be carried out in increments (preferably about 0.2 pH units) at regular intervals (preferably about 15 minutes). Acidification with hydrochloric acid is preferred, with concentrated aqueous hydrochloric acid (i.e., 35% hydrochloric acid or greater) most preferred.

The crystallization may also be carried out continuously, wherein the solution of captopril salt is added to a slurry of captopril while the slurry is maintained under acidic conditions. With a slow rate of addition, there is no tendency for the product to oil out of solution.

During acidification, the reaction temperature may be adjusted to aid crystal growth. Temperatures of about $20°$ to $45°$ C. are preferred. In addition, the solution may be seeded with captopril to aid crystal growth. Captopril may be further crystallized from the aqueous solution of the hydrolyzed substrate by cooling the solution. Cooling to about $0°$ to $4°$ C. is preferred.

An alternative to acidification is a hydrogen-supplying ion exchange resin. When a solution of compound IIIa is passed through the ion exchange resin, the $M^{\oplus}$ ions are exchanged with hydrogen, yielding a solution of captopril. Preferred resins are gel-type sulfonated polystyrene cation exchange resins, with 8 to 10% divinyl benzene cross-linking (e.g., Rohm & Haas Amberlite ® IR-120 and IR-122). The solution is then concentrated, whereupon captopril crystallizes out. The mother liquor and any filtration washes may be added to subsequent compound IIIa solutions. Such recycling of the uncrystallized solution minimizes product loss to waste streams.

The invention will now be described by the following working examples, which are meant to illustrate rather than limit the invention.

EXAMPLE 1

Under nitrogen atmosphere, a solution of 160 ml of 9.5 N sodium hydroxide was cooled to $0°$ to $2°$ C., and 128 g of 1-[S-3-(acetylthio)-2-methyl-1-oxopropyl]-L-proline (120 g on an anhydrous basis) was added while keeping the temperature no greater than $45°$ C. After about 5 minutes at $30°$ to $45°$ C., hydrolysis was complete as determined by HPLC, and the solution of the resulting captopril salt was acidified with 51 ml of concentrated hydrochloric acid to pH 7.3. The solution was polish-filtered at $45°$ C., and the equipment was rinsed with 21 ml of distilled water. The combined filtrates were acidified at $37°$ to $45°$ C. to pH 3.90 with 49 ml of concentrated hydrochloric acid, and seeded with 0.1 g of captopril. The suspension was cooled to about $32°$ C. to initiate good crystal growth, and held for about one hour. The suspension was acidified with concentrated hydrochloric acid every 15 minutes in increments of about 0.2 pH units until pH 3.0 was reached. Then the suspension was acidified to pH 1.8, and kept at $30°$ to $34°$ C. for about 30 minutes. The suspension was rapidly cooled to $0°$ to $4°$ C., and held at that temperature range for about 30 minutes. The product was filtered and washed with two-70 ml portions of cold water at about 4° C. Vacuum-drying at 40° C. yielded 88.0 g (90.5 M%) of captopril. Melting point: 103° to 107° C. Additional analytical data: 99.9% titration purity; 99.9% HPLC purity; 0.1% water. Disulfide content: 0.3%.

EXAMPLE 2

A solution of captopril salt was prepared in accordance with Example 1 and diluted with distilled water to 3.5N sodium ions (about 1.0M captopril salt). This feed solution (852 ml, pH 13.8) was passed at a rate of 200 ml/min through a column containing a gel-type sulfonated polystyrene cation exchange resin having 10% divinyl benzene crosslinking (Rohm & Haas IR-122). Distilled water was used to drive the feed solution through the column, and a total of 5 l was collected from the column outlet. The pH of the collected solution was 1.37.

The solution was concentrated to 315 ml, and the product crystallized and was filtered and dried. No cake wash was used in the isolation. The yield was 159.9 g (about 86M %).

The column was regenerated and the same procedure repeated. The mother liquor from the first pass was added to the collected effluent from the second pass, and the solution was concentrated to 315 ml. The product was crystallized, filtered and dried to yield 175.8 g (about 95M %).

A third pass was made, with the mother liquor from the second pass recycled back. Again, the yield was about 95M %.

What is claimed is:

1. A process for preparing a product of the formula

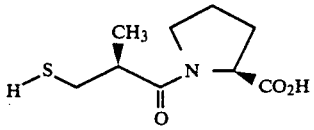

which comprises:
(a) reacting a substrate of the formula

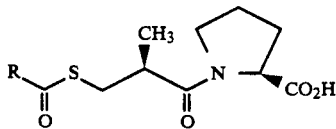

wherein R is lower alkyl or lower alkoxy with an aqueous solution of about 4M or greater of sodium hydroxide, lithium hydroxide or potassium hydroxide to form a reaction mixture comprising

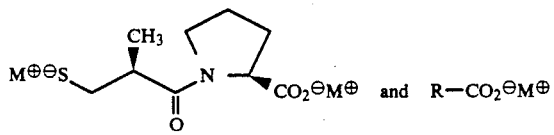

wherein M⊕ is a sodium, lithium or potassium ion; and
(b) neutralizing the reaction mixture to form the product.

2. The process of claim 1, wherein the neutralization is effected by passing the salt of the substrate through a hydrogen-supplying ion exchange resin.

3. The process of claim 1, wherein the neutralization is effected by acidification with a mineral acid.

4. The process of any one of claims 1 to 3, wherein R is methyl.

5. The process of any one of claims 1 to 3, wherein the process is carried out under an inert atmosphere.

6. The process of claim 4, wherein the process is carried out under an inert atmosphere.

7. The process of claim 1, wherein the sodium, lithium or potassium hydroxide solution has a concentration of about 4M to 18M.

8. The process of claim 1, wherein the sodium, lithium or potassium hydroxide solution has a concentration of about 9.5M.

9. The process of any one of claims 1, 7, or 8, wherein the aqueous solution of the sodium, lithium or potassium hydroxide comprises about 2.6 to 5 molar equivalents of sodium, lithium or potassium ions.

10. The process of claim 9, wherein the aqueous solution of the sodium, lithium or potassium hydroxide comprises about 3.3 molar equivalents of sodium, lithium or potassium ions.

11. The process of any one of claims 1, 7, or 8, wherein the aqueous solution comprises sodium hydroxide.

12. The process of claim 9, wherein the aqueous solution comprises sodium hydroxide.

13. The process of claim 10, wherein the aqueous solution comprises sodium hydroxide.

14. The process of claim 1, wherein the process is carried out at a temperature of about −10° to 50° C.

15. The process of any one of claims 1, 3, or 14, further comprising adjusting the neutralized substrate to a reaction temperature of about 20° to 45° C.

16. The process of claim 3, wherein the acidification is immediately effected to a pH of about 3.5 to 4.5.

17. The process of claim 16, wherein the acidification is immediately effected to a pH of about 3.9.

18. The process of any one of claims 16 or 17, wherein the reaction mixture is incrementally further acidified to a pH less than or equal to 3.

19. The process of claim 18, wherein the further acidification is effected in increments of 0.2 pH units at 15-minute intervals.

20. The process of any one of claims 3, 16, or 17, wherein the acidification is effected with hydrochloric acid.

21. The process of claim 18, wherein the acidification is effected with hydrochloric acid.

22. The process of claim 19, wherein the acidification is effected with hydrochloric acid.

23. The process of claim 20, wherein the acidification is effected with an aqueous solution having a hydrochloric acid concentration of 35% or greater.

24. The process of claim 21, wherein the acidification is effected with an aqueous solution having a hydrochloric acid concentration of 35% or greater.

25. The process of claim 22, wherein the acidification is effected with an aqueous solution having a hydrochloric acid concentration of 35% or greater.

26. The process of claim 2, wherein the hydrogen-supplying ion exchange resin comprises a polystyrene cation exchange resin having divinyl crosslinking.

* * * * *